United States Patent [19]

Haynes et al.

[11] Patent Number: 5,660,857
[45] Date of Patent: Aug. 26, 1997

[54] BIOPOLYMER COMPOSITES

[75] Inventors: Carla A. Haynes, Glasgow; Wilson Harvey; Paul W. Watt, both of Stirling, all of United Kingdom

[73] Assignee: Johnson & Johnson Medical Inc., Arlington, Tex.

[21] Appl. No.: 437,905

[22] Filed: May 10, 1995

Related U.S. Application Data

[62] Division of Ser. No. 35,001, Mar. 22, 1993.

[51] Int. Cl.$^6$ .................................. A61K 9/48; A61F 2/02
[52] U.S. Cl. ........................................ 424/450; 424/426
[58] Field of Search ............................... 424/423, 426, 424/450

[56] References Cited

U.S. PATENT DOCUMENTS

| | | |
|---|---|---|
| 3,632,361 | 1/1972 | Battista . |
| 3,823,212 | 7/1974 | Chvapil . |
| 4,265,233 | 5/1981 | Sugitachi et al. . |
| 4,312,675 | 1/1982 | Pickens et al. . |
| 4,320,201 | 3/1982 | Berg et al. . |
| 4,412,947 | 11/1983 | Cioca . |
| 4,533,358 | 8/1985 | Yoden et al. . |
| 4,571,422 | 2/1986 | Symes et al. . |
| 4,614,794 | 9/1986 | Easton et al. . |
| 4,670,550 | 6/1987 | Bleeker et al. . |
| 5,039,414 | 8/1991 | Mueller et al. . |
| 5,041,292 | 8/1991 | Feijen ........................ 424/484 |
| 5,073,378 | 12/1991 | Shoshan et al. . |
| 5,142,362 | 8/1992 | Masera et al. . |

FOREIGN PATENT DOCUMENTS

| | | |
|---|---|---|
| 1 205 609 | 9/1970 | European Pat. Off. . |
| 6652M | 3/1969 | France . |
| 55-84167 | 6/1980 | Japan . |
| 1 204 438 | 9/1980 | United Kingdom . |
| 2 058 084 | 4/1981 | United Kingdom . |
| 9 101 945 | 2/1991 | WIPO . |

OTHER PUBLICATIONS

Collagen Sponge: Theory and Practice of Medical Applications; J. Biomed. Materi. Res vol. 11, pp. 721–741 (1977) by Milos Chvapil.

Collagen Biomaterials Characteristics and Applications; JALCA, vol. 80, pp. 195–212 (1985), Alain Huc.

Derwent WPI Abstract JP-A-55082621, Jun. 21, 1980.

Derwent WPI Abstract JP-B-85034923, Jun. 25, 1980.

*Primary Examiner*—Carlos Azpuru
*Attorney, Agent, or Firm*—Andrew C. Farmer

[57] ABSTRACT

A process for preparing a composite comprising an insoluble protein matrix and an oleaginous material, which is useful as a material for surgical dressings and biomedical implants, and as a cosmetic material for application to the skin. The process comprises the steps of mixing a protein, the oleaginous material and water to form an emulsion of the oleaginous material in an aqueous dispersion of the protein, and subsequently drying or freeze-drying the emulsion to form a film or a sponge.

10 Claims, 2 Drawing Sheets

BIOPOLYMER COMPOSITES

CROSS-REFERENCE TO RELATED APPLICATIONS

This is a division of application Ser. No. 08/035,001, filed Mar. 22, 1993, which is hereby incorporated by reference.

BACKGROUND OF THE INVENTION

1. Field of the Invention

This invention relates to composites of an insoluble protein matrix with an oleaginous component, and to the preparation of such composites. Such composites are useful in a variety of applications, and particularly as materials for surgical dressings and biomedical implants, and as cosmetic materials for application to the skin.

2. Background Art

Biopolymers, such as animal proteins and plant polysaccharides, have been used in recent years in a number of diverse applications, including biomedical applications. For example, alginates (which are polysaccharides derived from seaweeds) are valuable for their haemostatic properties, while collagen (the major protein of skin and connective tissue) has been used in wound dressing materials, as well as in surgical sponges (see, for example, U.S. Pat. No. 3,632,361; U.S. Pat. No. 4,412,947; U.S. Pat No. 3,823,212; Chvapil, J. Biomed. Mater. Res. 11, 721 to 741 (1977); Huc, J. Am. Leather Chem. Assoc. 80, 195 to 212 (1985); and GB-A-2058084). Collagen is attractive in a biomedical context, principally because it is biocompatible, resorbable, structurally versatile and also has haemostatic properties.

Collagen sponges are known to be capable of absorbing large quantities of water. However, it has also been suggested in WO-A-9101945 that sponges of collagen or of certain other natural products can be used to absorb oils. In particular, it is suggested that such sponges can be used to separate and recover oils from aqueous media, and this is said to be of utility in treating offshore oil spills.

According to WO-A-9101945, collagen and gelatin sponges may be capable of absorbing in excess of 50 times their own weight of oil, and the absorbed oil may be recovered by squeezing or by other physical compression means. It is therefore believed that the absorbed oil is held predominantly or exclusively within the pores of the sponge.

Japanese laid-open patent application JP-A-55084167 (Lion Hamigaki KK) describes medicated sponge bands for the treatment of periodontal disease. The sponge bands comprise a sponge matrix of a soluble polymer having droplets of non-volatile oil dispersed therein. The non-volatile oil may contain dissolved medicaments. The sponge bands are formed by freeze drying an oil-in-water emulsion having the soluble polymer dissolved in the aqueous phase. The soluble polymers may be natural, synthetic or semi-synthetic polymers such as cellulose derivatives, natural gums, sodium alginate, gelatin or polyvinylpyrrolidone. In use, the medicated sponge bands are applied to affected areas such as mucous membranes in the oral cavity. The bands rapidly absorb water to form a sticky oil-in-water ointment. The sponge band is normally provided with an impermeable backing layer to improve the persistence of the ointment at the affected area.

SUMMARY OF THE INVENTION

The present invention is based on the discovery that a biopolymer matrix based on an insoluble protein can be formed with significant quantities of an oleaginous material held within the matrix itself (rather than physically entrapped within the pores of such a matrix), and that such a material exhibits a surprisingly non-oily or non-greasy appearance and feel.

According to the present invention, there is provided a process for preparing a composite comprising a matrix of an insoluble protein and an oleaginous material, said process comprising the steps of mixing a protein, the oleaginous material and water to form an emulsion of said oleaginous material in an aqueous dispersion of the protein and subsequently drying the emulsion.

In one embodiment, the emulsion is dried as a thin layer to form a film. The invention thus further provides a film comprising a composite of a matrix of an insoluble protein and an oleaginous material, the oleaginous material being distributed throughout the film as discrete microscopic droplets. Typically, the droplets have a maximum dimension less than 25 µm, and generally in the range 0.5 to 10 µm.

Drying to form a film may conveniently be carried out at a temperature of from 1° C. to 100° C., and more preferably at a temperature of from 15° to 60° C. In this embodiment, the emulsion preferably also includes a plasticiser to facilitate film formation. Suitable plasticisers include glycerol, sorbitol and polyethylene glycol, which will generally be used in amounts up to 40% by weight of the film. More preferably, the plasticiser constitutes from 5 to 30% by weight of the film. The film may optionally be perforated or reticulated.

In an alternative embodiment, the emulsion is frozen and then freeze dried, to form a sponge, the matrix of the sponge being formed of the insoluble protein/oleaginous material composite. In this embodiment, too, the oleaginous material may appear as discrete microscopic droplets when surface of the sponge matrix is viewed.

In yet other embodiments the composite is heteromorphic. That is to say, the composite is structurally and/or compositionally inhomogeneous. For example, a heteromorphic composite may be made by mixing flakes of a composite film according to the present invention into the oil-in-water emulsion followed by freeze drying the emulsion. This procedure results in a heteromorphic sponge having flakes of film composite embedded in a sponge matrix. Likewise, it is possible to make a laminated heteromorphic sponge having alternating layers of composite film and composite sponge.

In all of the above-described embodiments, the emulsion is preferably degassed to removed trapped air before it is dried.

The oleaginous material may be an oil, a grease, a fat or a wax. Preferably, the mixing of the protein, oleaginous material and water is carried out at a temperature at which the oleaginous material is liquid. Generally, the oleaginous material will be an oil at room temperature (eg. at 25° C.). Suitable oils include mineral oils and vegetable oils. In the case of composite films according to the invention, the oleaginous material is preferably a dispersible oil, such as Labrafil M2125 CS, manufactured by Gattefossé s.a., 36 chemin de Genas, 69800 Saint-Priest, France. Labrafil M2125 CS is a mixture of unsaturated polyglycolysed glycerides obtained by partial alcoholysis of maize oil. Films formed using such an oil according to the present invention have been found to give reduced shrinkage on drying, as compared with films formed using conventional oils.

Preferably, the protein used to form the aqueous dispersion is itself an insoluble fibrous protein. The aqueous dispersion is then an aqueous suspension of insoluble protein fibres, and drying the emulsion results directly in the composite having a matrix of insoluble protein.

In alternative embodiments, the protein is a water soluble protein such as gelatin and the aqueous dispersion is a solution of that protein. These embodiments then further comprise the step of adding a cross-linking agent such as HMDI (hexamethylene diisocyanate), water soluble carbodiimide or glutaraldehyde to the emulsion to cross-link the soluble protein and render it insoluble in the finished composite.

Suitable insoluble fibrous proteins preferred for the process of the invention may include the so-called structural fibrous proteins and derivatives thereof, such as insoluble collagen, keratin, fibrin and elastin.

Preferably, the insoluble fibrous protein is predominantly comprised of insoluble collagen, which may suitably be obtained from bovine skin. Such collagen preferably has a fibre length of from 0.005 to 5 mm, and more preferably from 0.01 to 3 mm. Conveniently, but not essentially, the collagen is swollen prior to use, either in acid or in alkali. Acid swelling is preferred, with optimum swelling occurring in the pH range 2 to 3.5. Organic acids (e.g. acetic acid, malic acid, lactic acid and citric acid) and mineral acids (e.g. hydrochloric acid and sulphuric acid) can be used, but organic acids are preferable since they facilitate greater swelling of the collagen.

In general, the insoluble fibrous protein content of the emulsion is in the range 0.01 to 10% w/v, and preferably in the range 0.3 to 5% w/v.

The ratio of oleaginous material to protein in the emulsion (and hence in the final product) depends upon the end use to which the product is to be put, and also on the physical form of the end product. If the product is to be used in the form of a sponge, the weight ratio of oleaginous material to insoluble protein is preferably in the range 0.001:1 to 100:1 and more preferably in the range 0.001:1 to 25:1. Still more preferably the weight ratio of oleaginous material to insoluble protein is in the range from 0.05:1 to 25:1.

If the product is to be used in the form of a film, the weight ratio of oleaginous material to insoluble fibrous protein is preferably in the range 0.001:1 to 20:1, more preferably from 0.001:1 to 10:1 and most preferably from 0.001:1 to 5:1.

It will be understood that composites according to the invention may contain both insoluble and soluble proteins and other, additional biopolymers such as polysaccharides. The maximum amount of oleaginous material which it is appropriate to employ may depend on the total amount of protein in the mixture.

Cross-linking agents, such as HMDI (hexamethylene diisocyanate), water soluble carbodiimide or glutaraldehyde, can also be added during the emulsion manufacture to cross link the insoluble fibrous protein, soluble protein or soluble polysaccharides present in the emulsion thus increasing the tensile strength of the resulting matrix.

Composites according to the present invention containing low quantities of oleaginous material are conveniently made by dissolving the oleaginous material in a volatile organic solvent, such as n-hexane, prior to forming the emulsion. This aids the dispersion of the oleaginous material throughout the matrix. The volatile solvent is then lost during the drying process leaving the oleaginous material dispersed as microdroplets throughout the matrix.

An emulsifier may sometimes be incorporated in the emulsion to produce a more homogeneous dispersion of oleaginous material throughout the protein matrix. However, the use of pepsin solubilized collagen, gelatin or a polysaccharide in addition to the insoluble protein generally avoids the need for a separate emulsifier, and this is preferred for biomedical applications. For cosmetic applications, a wide range of commercially available emulsifiers may be used, such as lecithins, mono and diglycerides of fatty acids, and sorbitan esters.

It has also been found, surprisingly, that insoluble fibrous proteins are effective emulsifiers in aqueous suspension. Stable oil-in-water emulsions can be prepared for example by homogenising aqueous suspensions of insoluble protein fibres such as insoluble collagen fibres with oil at high shear to produce microdroplets of the oil dispersed between the protein fibres. The collagen fibres may be acid-swollen as described above. The insoluble protein content of the emulsions can range from 0.5% to 15% by weight of the emulsion, but is preferably from 1% to 10% by weight. The oil content can range from 1% to 50% by weight of the emulsion but is preferably 10% to 35% by weight.

When a separate emulsifier is used to form the emulsions according to the present invention, it is preferably used in the emulsion in an amount from 0.01 to 10% w/v. It will be understood, however, that the precise amount of emulsifier used will depend on the amount of oleaginous material used, the type of emulsifier, and the overall total dilution.

The composites of the present invention may be used as controlled release vehicles for pharmaceutically active agents. For this purpose, the composite may be applied as a wound dressing or as an implant. The pharmaceutically active agents which may be employed include hydrophobic agents and hydrophilic agents.

Hydrophobic pharmaceutically active agents, which may be dissolved in the oleaginous phase, include steroids (such as testosterone and oestradiol) and retinol. Hydrophilic pharmaceutically active agents include antibiotics (such as penicillins and cephalosporins), antiseptics (such as chlorhexidine), β-blockers (such as propanolol), and peptide hormones and growth factors. In some cases, these may be suspended in the oleaginous material (e.g. in particulate, crystalline form), and release of the agent in this case will depend on partitioning into the "aqueous" phase, i.e. the insoluble protein matrix. In other cases, the hydrophilic agents may be incorporated directly into the insoluble protein matrix, when the rate of their release is modified by the presence of droplets of the oleaginous material. A preferred such hydrophilic active agent is micronised mannose-6-phosphate.

In a further alternative embodiment, the emulsion is formed into beads or microspheres. This can be achieved by freezing droplets of the emulsion in liquid nitrogen and lyophilising as described in U.S. Pat. No. 4,837,285. Alternatively, microspheres can be prepared by forming a dispersion of the oil in water biopolymer emulsion in a water immiscible solvent/organic phase. Following addition of a cross linking agent, the biopolymer/oil emulsion particles are separated from the continuous solvent phase and the particles are dried, preferably by lyophilisation as described in either WO 9210287 or WO 9106286.

The composites of the invention are particularly useful as wound dressings or implants or as dressings specifically for the treatment of burns. The hydrophobic nature of the material (the degree of hydrophobicity is dependant on the content of the oleaginous phase) may be used to reduce moisture loss from wounds, to reduce trauma on removal, or to deliver active agents to the wound site. In these wound dressings or implants, factors which may promote wound healing can be incorporated into the matrix, these include growth factors, glycosaminoglycans (GAGS) such as hyaluronic acid, chondroitin sulphate or the low molecular weight heparins. Furthermore additional factors which have potential to reduce wound scarring such as mannose-6-phosphate, TGF-$\beta_3$, and anti TGF $\beta_1$ and $\beta_2$ can be dissolved/suspended in either the hydrophobic or hydrophilic phases of these matrices.

An additional application for the insoluble protein/oil films is as medicated implants for the treatment of periodontitis. As previously mentioned, these films can incorporate either hydrophobic or hydrophilic active agents. By controlling the quantity of the oleaginous material and the size and heterogeneity of the oil micro droplets, the delivery of both types of actives can be manipulated and controlled.

Furthermore, although not essential, the insoluble protein/ oil films can be reinforced by incorporating a biodegradable or non-biodegradable mesh. This supporting mesh can be, for example, and oxidised regenerated cellulose mesh such as Surgicel™ or a polylactate polyglycolate mesh such as Vicryl™. Incorporation of this mesh will increase the rigidity of the film making it easier to apply.

As already mentioned, the composites of the present invention are surprisingly non-oily and non-greasy to the touch. Only small amounts of the oleaginous material are released from the composites of the invention by squeezing, compared with the proportionately higher quantities of oil which are released from the sponges disclosed in WO-A-9101945. At least 90% by weight of the composites according to the present invention may be the stable, non-exuding oil phase. Insoluble protein—oil composites containing up to 70% by weight of dispersed oil feel non-oily when touched or gently squeezed.

The use of insoluble protein to form the matrix offers a number of surprising advantages over the use of soluble polymers as described in JP-A-55084167. First, the composites formed from insoluble proteins have excellent structural integrity when wetted in the wound dressing environment. The composites according to the present invention do not absorb water to form a sticky ointment. Instead, the composites according to the present invention maintain their integrity thereby providing support and protection to the wound. The composites according to the present invention degrade slowly in the wound, thereby releasing active agents into the wound at a controlled rate over an extended period. The composites according to the present invention are non-adhesive and readily removable from the wound with minimum wound trauma.

BRIEF DESCRIPTION OF THE DRAWINGS

The invention is now further described with reference to the following examples, and to the Figures, in which.

DESCRIPTION OF THE PREFERRED EMBODIMENTS

Example 1: Insoluble Collagen/Oil Sponge

A. Preparation of Fibrous Collagen from Hide

The insoluble collagen used in the emulsion preparation is preferably collagen which is pre-washed and rendered largely free of fat, non-collageneous proteins, polysaccharides and other carbohydrates as described in U.S. Pat. No. 4,614,794 or U.S. Pat. No. 4,320,201 or British Patent Spec. No. 1 204 438. The collagen is suspended in clean deionised pyrogen free water and homogenised to a fine fibrous suspension by passage through a homogenising system. Suitable homogenising systems are described in U.S. Pat. No. 4,320,201. Homogenising may be continued until a desired degree of fibre division is achieved. This results in a preferred fibre size of between 0.01 and 10 mm. The collagen can then be used in this form (as an aqueous slurry) or freeze dried and milled to form a dehydrated or partially hydrated mass of fibres.

B. Preparation of Sponge

The following components were used to prepare an insoluble collagen:oil sponge at a ratio of 1:10

| | |
|---|---|
| Biomedical grade fibrous collagen powder | 1.2 g |
| Soluble collagen in 0.05M acetic acid (4 mg/ml) | 150 ml (0.6 g) |
| Acetic acid 0.05M | 432 ml |
| Vegetable oil | 18 g |

The components were chilled to 4° C. and placed in a Waring Blendor. The mixture was homogenised three times at high speed for 30 secs before degassing in a vacuum chamber at <5 torr. The emulsion was then poured into an aluminium tray (255×500 mm) to give a thickness of 4 mm. The sample was blast frozen at −30° C. before freeze drying.

Example 2: Collagen/Oil Sponge

Figure 1:
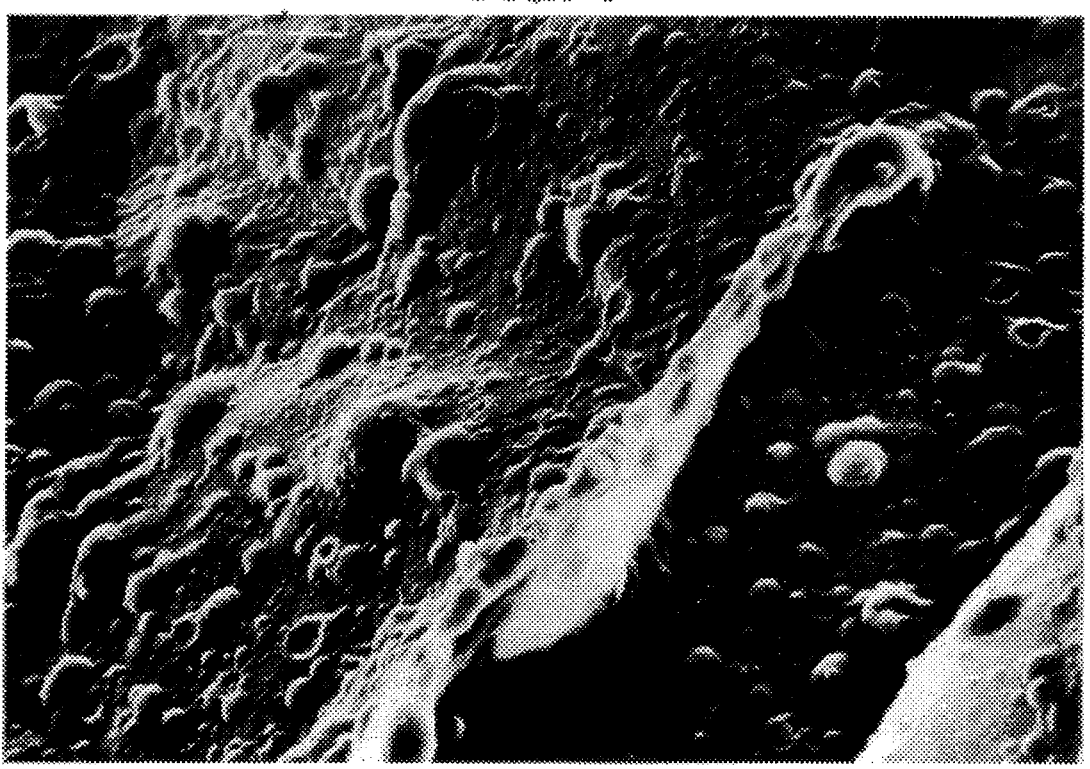
FIG. 1 is a scanning electron micrograph of an insoluble collagen/oil sponge according to the invention.

The procedure of example 1 was followed, but with an oil:collagen ratio of 2:1 (w/w). FIG. 1 shows a scanning electron micrograph of the resulting sponge at a magnification of 1100×. Discrete oil droplets can clearly be seen under the surface of the collagen matrix.

Example 3: Insoluble Collagen/Oil Film

The following components were used to prepare a collagen:oil film at a ratio of 1:2

| | |
|---|---|
| Biomedical grade fibrous collagen powder | 1.2 g |
| Soluble collagen in 0.05M acetic acid (4 mg/ml) | 150 ml (0.6 g) |
| Acetic acid 0.05M | 446.4 ml |
| Vegetable oil | 3.6 g |
| Glycerol | 0.12 g |

The components were chilled to 4° C. and placed in a Waring Blendor. The mixture was homogenised three times at high speed for 30 secs before degassing in a vacuum chamber at <5 torr. The emulsion was then poured into a PVC tray (320×500 mm) and placed in a chamber and air dried at room temperature.

Figure 2:
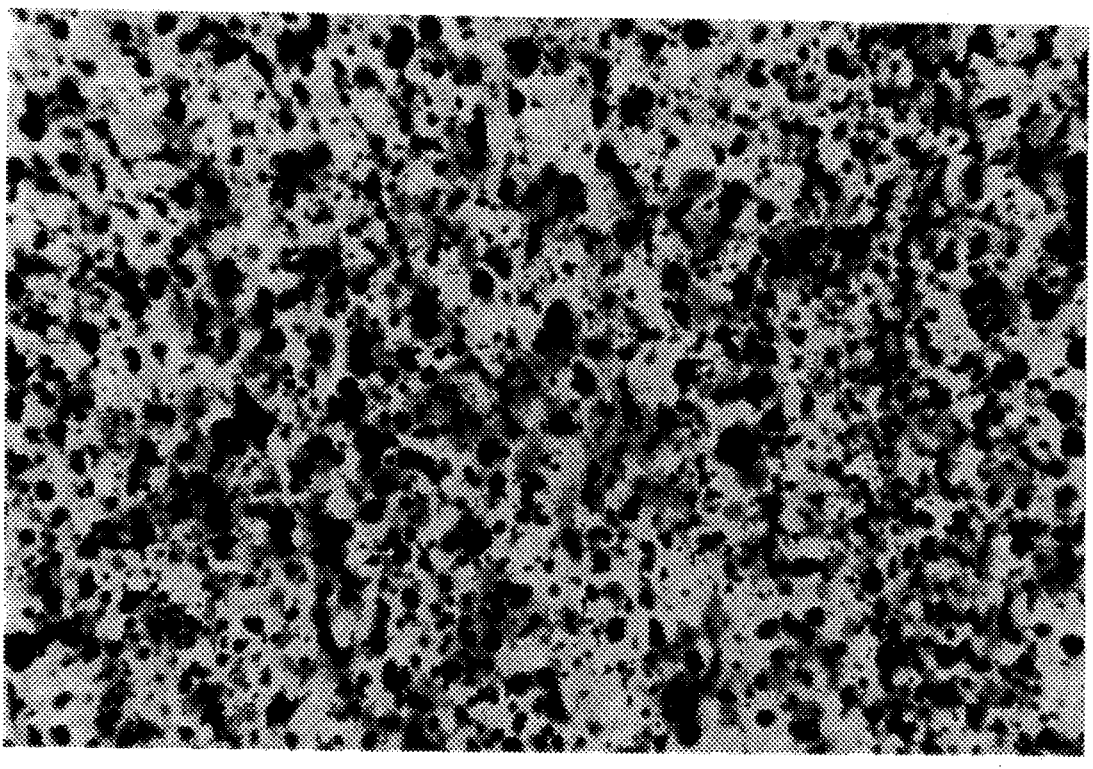
FIG. 2 is a light micrograph of an insoluble collagen/oil film according to the invention.

FIG. 2 shows the resulting film at a magnification of 750×. As with FIG. 1, discrete oil droplets (which have been stained with Sudan black) can be seen on the surface of the collagen.

Example 4: Crosslinked Collagen/Oil Sponge

The following components were used to prepare an oil-collagen HMDI crosslinked sponge at a ratio of 1:2.

| Insoluble fibrous collagen | 3 g |
| --- | --- |
| Mineral oil | 6 g |
| HMDI | 0.06 g |
| Deionised water | 594 ml |

The components were chilled to 4° C. and placed in a Waring Blendor. The mixture was homogenised at low speed for 30 secs while the HMDI cross linker (dispersed in a small volume of water and surfactant (marlophen)) was added. The homogenisation was continued at high speed for a further 60 secs. The slurry was then degassed in a vacuum chamber at <5 torr. The emulsion was then poured into trays, blast frozen and freeze dried.

Example 5: Collagen/Dispersible Oil Film

The following components were used to prepare a collagen:Labrafil M2125 CS oil film at a ratio of 1:2, using the procedure of Example 3:

| Biomedical grade fibrous collagen powder | 1.2 g |
| --- | --- |
| Soluble collagen in 0.05M acetic acid (4 mg/ml) | 150 ml (0.6 g) |
| Acetic acid 0.05M | 446.4 ml |
| Labrafil M2125 CS | 3.6 g |
| Glycerol | 0.12 g |

The use of a dispersible oil was found to produce a film which dried with less shrinkage and curling, as compared with the film of Example 3.

Example 6: Film Extrusion

As an alternative to drying the emulsion on trays for film production, an extrusion technique can be used. Following the degassing stage, an emulsion prepared as in Example 2 was transferred to an extruder. The emulsion was maintained at a maximum temperature of 19°±4° C. and extruded at 345 kPa (50 psi) onto a PTFE (polytetrafluoroethylene) coated glass fibre belt. The film was then batch dried on the conveyor at 45° C. for approximately 20 mins.

Example 7: Collagen/Oil Microspheres

The following components were used to prepare collagen/oil microspheres at a ratio of 1:1.

| Insoluble fibrous collagen | 1.8 g |
| --- | --- |
| Acetic acid (0.01M) | 598.2 ml |
| Mineral oil | 1.8 g |

The components were chilled to 4° C. and placed in a Waring Blendor. The mixture was homogenised at high speed for a total of 90 secs. The slurry was then degassed in a vacuum chamber at <5 torr. The emulsion was then used to prepare microspheres by the method described in U.S. Pat. No. 4,837,285 and lyophilised.

Example 8: Medicated Collagen-Alginate/Oil Film for the Treatment of Periodontitis The following components were used to prepare a chlorhexidine medicated collagen-alginate/oil film for the treatment of periodontitis. Collagen-alginate : oil ratio is 1:5.

| Fibrous insoluble collagen | 1.62 g |
| --- | --- |
| Sodium alginate | 0.18 g |
| Chlorhexidine digluconate | 1.8 g |
| Vegetable oil (Sesame oil) | 1.5 g |
| 0.05M acetic acid | 598.5 ml |
| Glycerol | 0.12 g |

The sodium alginate was dissolved in the acetic acid containing the glycerol and the chlorhexidine was added to this solution during homogenisation in a Waring Blendor at low speed. The collagen and oil were then added and the components were homogenised at high speed for a total of 90 secs. The emulsion was then degassed in a vacuum chamber at <5 torr before pouring the emulsion into a PVC tray (320 mm×500 mm) and air drying at room temperature. The resulting medicated film was then cut into strips 2×10 mm.

The above examples are intended for the purpose of illustration only. Many other processes and compositions according to the present invention as defined in the accompanying claims will be apparent to the skilled reader.

We claim:

1. A process for preparing a composite comprising an insoluble protein matrix and an oleaginous material, said process comprising the steps of mixing a protein, the oleaginous material and water to form an emulsion of said oleaginous material in an aqueous dispersion of the protein, and subsequently drying the emulsion, thereby producing a composite material comprising the protein and the oleaginous material.

2. The process of claim 1, wherein the mixing of the protein, oleaginous material and water is carried out at a temperature at which the oleaginous material is liquid.

3. The process of claim 1, wherein the oleaginous material is selected from the group consisting of mineral oils, vegetable oils, and mixtures thereof.

4. The process of claim 1, wherein the emulsion is dried as a thin layer to form a film.

5. The process of claim 1, wherein the emulsion is freeze dried, to form an insoluble protein based sponge.

6. The process of claim 1, wherein the weight ratio of oleaginous material to protein in the emulsion is in the range 0.00:1 to 100:1.

7. The process of claim 1 further comprising the step of adding a cross-linking agent to the emulsion.

8. The process of claim 1, wherein the protein comprises an insoluble fibrous protein.

9. The process of claim 8, wherein the insoluble fibrous protein is selected from the group consisting of insoluble collagen, keratin, fibrin, elastin, and mixtures thereof.

10. The process of claim 8, wherein the insoluble fibrous protein consists essentially of acid-swollen collagen.

* * * * *